US012708876B2

(12) United States Patent
Banchieri et al.

(10) Patent No.: US 12,708,876 B2
(45) Date of Patent: Aug. 18, 2026

(54) CELL RETENTION DEVICE

(71) Applicant: Sunflower Therapeutics, PBC, Hingham, MA (US)

(72) Inventors: Andrew Banchieri, Fremont, CA (US); Flora Liu, Boston, MA (US); Marc Miller Graham, Somerville, MA (US)

(73) Assignee: Sunflower Therapeutics, PBC, Hingham, MA (US)

(*) Notice: Subject to any disclaimer, the term of this patent is extended or adjusted under 35 U.S.C. 154(b) by 0 days.

(21) Appl. No.: 18/471,468

(22) Filed: Sep. 21, 2023

(65) Prior Publication Data

US 2024/0009625 A1 Jan. 11, 2024

Related U.S. Application Data

(63) Continuation of application No. 17/468,094, filed on Sep. 7, 2021, now Pat. No. 11,801,477.

(Continued)

(51) Int. Cl.

*B01D 63/06* (2006.01)
*B01D 69/02* (2006.01)

(Continued)

(52) U.S. Cl.

CPC ........... *B01D 63/065* (2013.01); *B01D 69/02* (2013.01); *B01D 69/107* (2022.08);

(Continued)

(58) Field of Classification Search

CPC .... B01D 63/065; B01D 69/02; B01D 69/107; B01D 69/108; B01D 71/16; B01D 71/34;

(Continued)

(56) References Cited

U.S. PATENT DOCUMENTS 3,390,774 A * 7/1968 Neely .................... B01D 27/06 210/132
4,476,022 A * 10/1984 Doll ....................... B01D 65/08 210/321.83

(Continued)

FOREIGN PATENT DOCUMENTS

CN 105 195 022 A 12/2015
EP 0251620 A2 1/1988

(Continued)

OTHER PUBLICATIONS

Crowell et al., "On-demand manufacturing of clinical quality biopharmaceuticals", Nature Biotechnology, Received Nov. 16, 2017; accepted Aug. 27, 2018; published online Oct. 1, 2018; http://dx.doi.org/10.1038/nbt.4262, 15 pages.

(Continued)

*Primary Examiner* — Pranav N Patel

(74) *Attorney, Agent, or Firm* — Morgan, Lewis & Bockius LLP

(57) ABSTRACT

A cell retention device includes a structured support with a plurality of circumferentially distributed ribs to retain the active filtering surface of a flexible, porous membrane filter medium. The filter medium surrounds the support in contact with the peaks of the ribs, thereby forming axial voids between the rib peaks. This arrangement imparts sufficient structural support over small regions of the filter medium to facilitate its use in a circular (or other rounded) configuration while providing sufficient channel volume to support high throughput of fluid sparse of cells.

15 Claims, 3 Drawing Sheets

Related U.S. Application Data

(60) Provisional application No. 63/075,443, filed on Sep. 8, 2020.

(51) Int. Cl.

| | |
|---|---|
| ***B01D 69/10*** | (2006.01) |
| ***B01D 71/16*** | (2006.01) |
| ***B01D 71/34*** | (2006.01) |
| ***B01D 71/50*** | (2006.01) |
| ***B01D 71/68*** | (2006.01) |
| ***C12M 1/00*** | (2006.01) |
| ***C12M 1/12*** | (2006.01) |

(52) U.S. Cl.

CPC .......... *B01D 69/108* (2022.08); *B01D 71/16* (2013.01); *B01D 71/34* (2013.01); *B01D 71/50* (2013.01); *B01D 71/68* (2013.01); *C12M 23/06* (2013.01); *C12M 29/04* (2013.01); *C12M 47/02* (2013.01); *C12M 47/04* (2013.01); *B01D 2325/0283* (2022.08); *B01D 2325/20* (2013.01)

(58) Field of Classification Search

CPC .................... B01D 71/50; B01D 71/68; B01D 2325/0283; B01D 2325/20; B01D 61/14; B01D 71/10; B01D 2313/06; B01D 2313/08; B01D 2313/12; B01D 63/06; B01D 69/10; C12M 23/06; C12M 29/04; C12M 47/02; C12M 47/04; C12M 33/14; C12M 41/40

See application file for complete search history.

(56) References Cited

U.S. PATENT DOCUMENTS

| | | | | |
|---|---|---|---|---|
| 4,735,717 | A * | 4/1988 | Sims | B01D 53/22 210/247 |
| 4,755,300 | A * | 7/1988 | Fischel | B01D 63/16 436/178 |
| 5,174,896 | A | 12/1992 | Harms, II | |
| 5,820,767 | A | 10/1998 | Kane et al. | |
| 5,906,737 | A * | 5/1999 | Hoeppner | B01D 29/111 210/232 |
| 6,875,342 | B2 | 4/2005 | Shane | |
| 8,225,940 | B2 | 7/2012 | Schmidt | |
| 8,435,781 | B2 | 5/2013 | Kodama | |
| 9,908,069 | B2 | 3/2018 | Galifi | |
| 10,358,626 | B2 | 7/2019 | Cattaneo et al. | |
| 2001/0010297 | A1* | 8/2001 | Pulek | B01D 29/111 210/493.2 |
| 2004/0055939 | A1 | 3/2004 | Wybo | |
| 2007/0138082 | A1 | 6/2007 | Connors, Jr. et al. | |
| 2010/0320138 | A1 | 12/2010 | Waller, Jr. et al. | |
| 2011/0117639 | A1 | 5/2011 | Suazo et al. | |
| 2011/0180474 | A1 | 7/2011 | Bowman | |
| 2011/0284444 | A1 | 11/2011 | Chen | |
| 2012/0261333 | A1 | 10/2012 | Moran et al. | |
| 2014/0131270 | A1* | 5/2014 | Zeiler | B01D 63/14 210/493.1 |
| 2014/0291231 | A1 | 10/2014 | Wöstmann et al. | |
| 2015/0343341 | A1* | 12/2015 | Carrion | B01D 29/54 210/338 |
| 2018/0133655 | A1* | 5/2018 | Brown | A61M 1/025 |
| 2018/0272286 | A1* | 9/2018 | Gronwald | B01D 69/141 |
| 2019/0134541 | A1 | 5/2019 | Reardon | |
| 2019/0247560 | A1* | 8/2019 | Storr | A61M 1/3496 |

FOREIGN PATENT DOCUMENTS

| | | | |
|---|---|---|---|
| EP | 2223724 | B1 | 7/2014 |
| EP | 2286919 | B1 | 6/2017 |
| JP | 60-061018 | A | 4/1985 |
| JP | 2007236665 | A | 9/2007 |
| JP | 2014097492 | A | 5/2014 |
| WO | 2018132512 | A1 | 7/2018 |
| WO | 2018183848 | A1 | 10/2018 |
| WO | 2018183971 | A1 | 10/2018 |
| WO | 2018183972 | A2 | 10/2018 |
| WO | 2019060638 | A1 | 3/2019 |
| WO | 2019147310 | A2 | 8/2019 |

OTHER PUBLICATIONS

Matthews et al., "Development of a general defined medium for Pichia pastoris", Biotechnology and Bioengineering. 2018;115:103-113.

International Search Report and the Written Opinion for corresponding International Patent Applicant No. PCT/US2021/049251 dated Dec. 21, 2021,8 pages.

Supplementary European Search Report for corresponding European Patent Application No. EP 21 86 7429 dated Sep. 3, 2024, 2 pages.

* cited by examiner

CELL RETENTION DEVICE

CROSS REFERENCE TO RELATED APPLICATIONS

This application is a continuation of U.S. patent application Ser. No. 17/468,094, filed on Sep. 7, 2021, which claims priority to and the benefit of, and incorporates herein by reference in its entirety, U.S. Ser. No. 63/075,443, filed on Sep. 8, 2020, the entire disclosure of each is hereby incorporated by reference.

FIELD OF THE INVENTION

The present invention relates, generally, filtering and retaining microorganisms grown in a bioreactor.

BACKGROUND

Biopharmaceuticals and vaccines are commonly produced in bioreactor systems designed to maintain the viability and productivity of cells in fluid media. Adding and removing the media from the bioreactor and separating the cells from the fluids represent critical aspects of the processes for manufacturing. Typical processes for cell culture or fermentation involve the addition of media in a fixed bolus for a batch of fluid or in a set of repeated quantities of media for a fed-batch process. There are substantial advantages to providing media continuously to a bioreactor to enhance viability of cells, productivity, quality of recombinantly expressed proteins or all three. To maintain a continuous feed into the bioreactor, it is generally necessary to remove fluid or cells or both from the bioreactor at a similar rate as that which fluid is added to the reactor to avoid overflowing. It may be preferred to remove the fluid sparse of cells to maintain high cell densities in the reactor in the operational mode called perfusion.

Filtering cells from the fluid in the bioreactor is an essential step to enable continuous operation of the bioreactor. The filter must allow fluids in the reactor to pass through while rejecting cells and particulate matter. To draw the fluid sparse of cells from a bioreactor, a filter component, fluidic connections such as tubing, and a pump may be employed. Additional elements may include a pressure sensor, flow sensor, or other in-line sensors to monitor the flow of fluid. System components may be intended for a single use or may instead be tolerant of chemical, oxidative, heat, light, or other methods for sanitization.

The ability of the filter component to achieve the segregation of a fluid from cellular and particulate matter is critical. A common design is a filter device positioned external to the reactor and connected by one or more fluidic connectors and pumps. Fluid from the bioreactor dense with cells may be circulated through a filtering device wherein the permeate is recovered sparse of cells and the retained cells are returned to the reactor. The directionality of the retentate flow may be circular or alternating. An external configuration simplifies the set-up and cleaning of the reactor or replacement of the filter during operations if clogged. For cell culture with mammalian cells, this configuration of the filtering system is commonly used.

Manufacture of biopharmaceuticals and vaccines may involve other eukaryotic and prokaryotic microorganisms such as yeast, fungi, algae, diatoms, and bacteria. These alternative host cells for production typically have faster growth rates and higher respiration requirements than mammalian cells. For these reasons, external circulation of cells from the bioreactor is less desirable than filtering devices positioned inside a bioreactor. Moreover, the limited space available inside a bioreactor for these elements would add a physical constraint to the design were an internal filter to be employed.

Openings in a reactor are typically available in discrete numbers based on the size of the reactor, and with diameters of standard sizes. This configuration commonly motivates a cylindrical design for the filter to fit in the reactor. Dense hollow fibers may be bundled into a cylindrical form, for example. A second approach is to use ceramic filtering elements positioned in the reactor. In some designs, the filter is integrated with other components in the reactor such as the impeller shaft.

Hollow fiber filters comprising a plurality of filtering membranes provide large nominal surface areas. One limitation of these designs for microbial perfusion is limited access to the internal surfaces of the fibers when the densities of cells in the reactor become high, a preferred state for optimizing productivity of the bioreactor. Alternative designs with structured and spaced fibers can overcome this limitation albeit with reduced total surface area compared with dense bundles of fibers and complex manufacturing requirements to produce these designs.

Ceramic filters provide a fixed surface area and can be configured in a cylindrical design to fit inside of a bioreactor. Other configurations can use disks. The filtering properties of the ceramic materials are appropriate for separating cells from the fluid in the bioreactor, but the manufacture of large ceramic designs is expensive and production in large numbers may be challenging. The materials are also brittle and susceptible to breaking or cracking during installation or operation.

Other widely available filtering materials, such as polymeric membranes, feature appropriate porosity for filtering cells, suitability for use in biopharmaceutical production, and compatibility with methods for sterilization or sanitization. Polymeric membranes are often used in planar configurations for filters external to a bioreactor or other operation in purification or recovery of biological materials. Fragile and often thin, these materials are generally unsuited to a cylindrical configuration; if wrapped like a tube, for example, pumping fluids in or out of the membrane will create significant radial stresses that can overwhelm its mechanical stability. Accordingly, there is a need for filters with form factors suitable for in-reactor deployment, which can withstand the rigors of use, and which may be conveniently and inexpensively manufactured.

SUMMARY

Embodiments of the present invention utilize a structured support with a plurality of circumferentially distributed ribs to retain the active filtering surface of a flexible, porous membrane filter medium. The filter medium surrounds the support in contact with the peaks of the ribs, thereby forming axial voids between the rib peaks. This arrangement imparts sufficient structural support over small regions of the filter medium to facilitate its use in a circular (or other rounded) configuration while providing sufficient channel volume to support high throughput of fluid sparse of cells.

Accordingly, in a first aspect, the invention relates to a filter comprising, in various embodiments, an elongated nonporous element having a plurality of axial ribs circumferentially distributed around an exterior portion thereof; the ribs have radial peaks and radial recessions therebetween. The filter also comprises a membrane filter medium surrounding the exterior portion of the nonporous element in contact with the peaks of the ribs, thereby forming a plurality of axial voids between the radial recessions and the membrane filter medium; a central channel extending axially through at least a portion of the nonporous element and terminating in an outlet; and at least one radial channel fluidically coupling the axial voids to the central channel, whereby negative pressure at the outlet propagates through the axial channels to the membrane filter medium.

In some embodiments, the elongated element is substantially or fully nonporous. In other embodiments, the elongated element has pores sized to exclude cells and selectively allow proteins and fluids to pass. The pores may have diameters ranging from 10 nm to 5 μm and/or may be sized to allow proteins having weights up to 500 kDa to pass.

In various embodiments, the radial channel(s) have a first end opening into the central channel and a second end opening into an annular region radially recessed relative to the ribs. The annular region may be unribbed and may have a plurality of circumferentially distributed radial channels therethrough. In some embodiments, the elongated element includes a plurality of unribbed annular regions each having a plurality of circumferentially distributed radial channels therethrough.

In various embodiments, the filter medium is one or more of cellulose ester, polyethersulfone, cellulose acetate, polyvinylidene fluoride or polycarbonate. The nonporous element may have a substantially circular cross-section.

In some embodiments, the radial peaks each have a radial height approximately equal to its circumferential width. The ratio of the diameter of the central channel to the diameter of the elongated element with the membrane filter medium wrapped therearound may range from 0.1 to 0.95 (e.g., 0.75). The length of the elongated element may be related to the diameter of the elongated element with the membrane filter medium wrapped therearound; for example, the ratio of the element length to this diameter may be approximately 3.0.

As used herein, the term "approximately" means±10%, and in some embodiments, ±5%. Reference throughout this specification to "one example," "an example," "one embodiment," or "an embodiment" means that a particular feature, structure, or characteristic described in connection with the example is included in at least one example of the present technology. Thus, the occurrences of the phrases "in one example," "in an example," "one embodiment," or "an embodiment" in various places throughout this specification are not necessarily all referring to the same example. Furthermore, the particular features, structures, routines, steps, or characteristics may be combined in any suitable manner in one or more examples of the technology. The headings provided herein are for convenience only and are not intended to limit or interpret the scope or meaning of the claimed technology.

BRIEF DESCRIPTION OF THE DRAWINGS

The foregoing and the following detailed description will be more readily understood when taken in conjunction with the drawings, in which.

DETAILED DESCRIPTION

Figure 1:
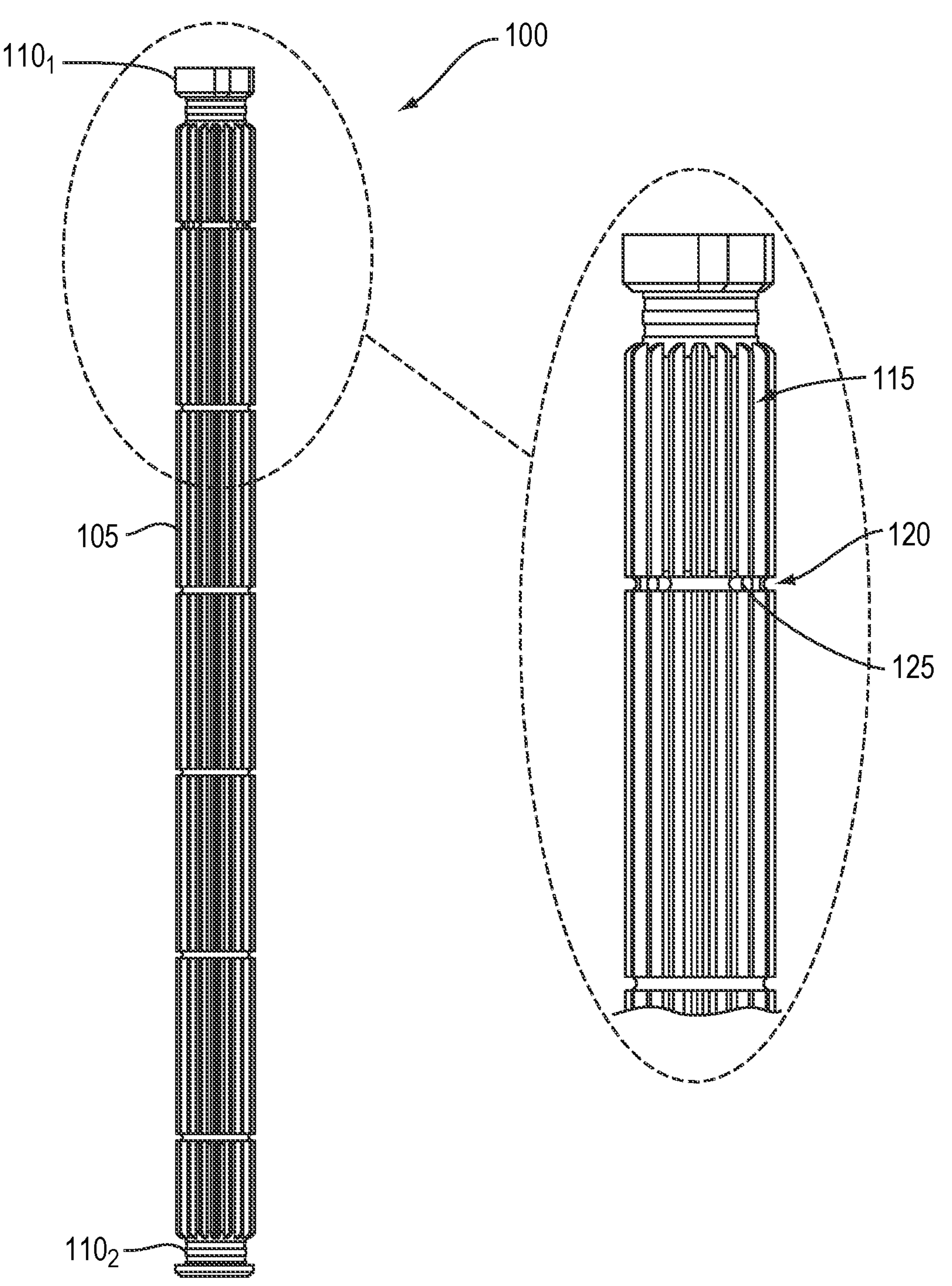
FIG. 1 is an elevation of a support in accordance with embodiments of the invention.

Refer first to FIG. 1, which illustrates a support 100 that includes a stacked series of longitudinal segments collectively indicated at 105, and terminating in first and second opposed ports or outlets 1101, 1102. In some embodiments, the support 100 includes only one outlet 110. The support 100 also includes a series of axial, circumferentially distributed ribs 115 interrupted by one or more radially recessed annular regions 120. The recessed regions 120 each contain one or more bores 125 leading to an interior central channel discussed in greater detail below. The support 100 may be fabricated using any suitable method (e.g., molding, etching, 3D printing, etc.) from any suitable durable, solid, nonporous material such as stainless steel or other metal, highly crosslinked polymer, or ceramic material. Examples of suitable materials include cellulose acetate (CA), polycarbonate, cellulose ester (CE), polyethersulfone (PES), or modified polyethersulfone (mPES). Such materials are herein referred to as "fully nonporous." Some porosity may be acceptable so long as the pores are sized to exclude cells and selectively allow proteins or other components in the fluids to pass. These pores may be sized from 10 nm to 5 μm. The pores may allow proteins of 5 kDa, 10 kDa, 20 kDa, 30 kDa, 40 kDa, 50 kDa, 60 kDa, 70 kDa, 80 kDa, 90 kDa, 100 kDa, 110 kDa, 120 kDa, 130 kDa, 140 kDa, 150 kDa, 160 kDa, 170 kDa, or up to 500 kDa, or any weight in between these values to pass. In some embodiments, the pore sizing is selected to be 0.22 μm, 0.45 μm, 0.9 μm, 1 μm, 2 μm, 5 μm, or any diameter in between these values. Such materials are herein referred to as "substantially nonporous."

Figure 2A:
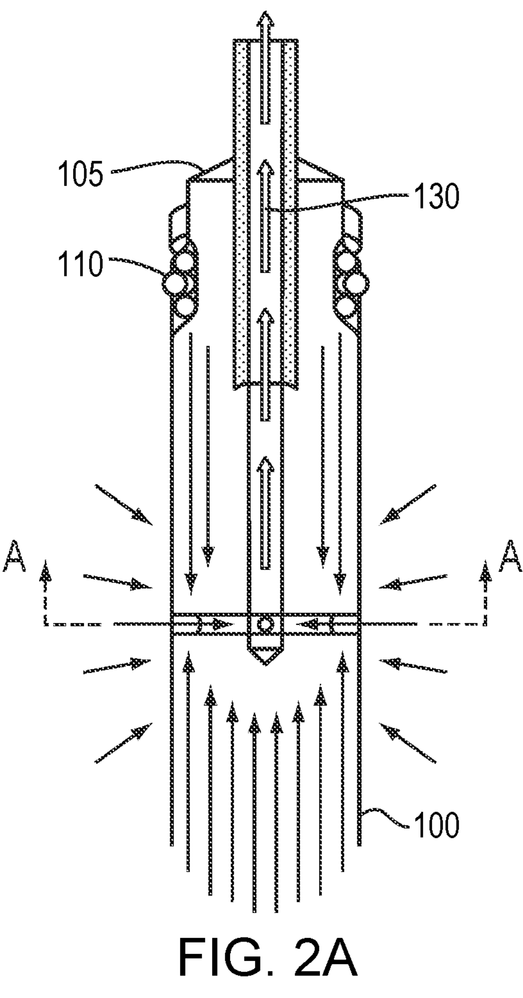
FIG. 2A is a sectional view of a portion of the axial length of the support shown in FIG. 1.
Figure 2B:
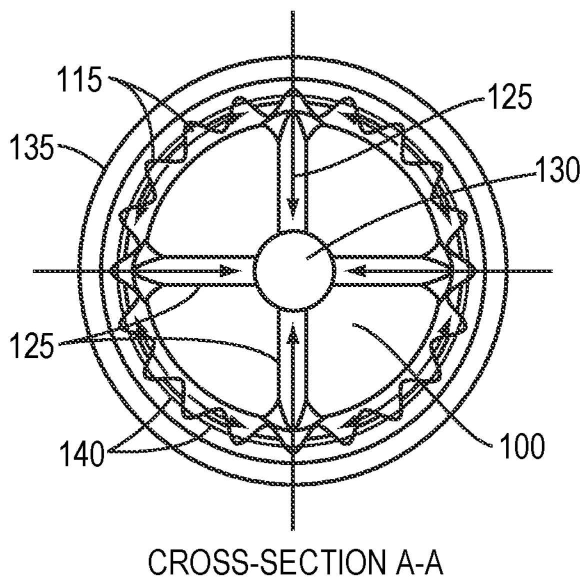
FIG. 2B is a transverse sectional view of the support shown in FIG. 1, taken along the line A-A in FIG. 2A.

FIGS. 2A and 2B illustrate the central interior channel 130 extending through at least a portion of the axial length of the support 100, i.e., with reference to FIG. 1, at least from an outlet 110 to the radial bores 125 of the sole or distal recessed region 120. A membrane filter 135 surrounds the support 100, its interior surface resting against the peaks of the ribs 115 to form axial voids 140 along the support 100. These voids 140 are in fluid communication with the recessed region(s) 120 and, hence, with the central channel 130 via the radial bores 125.

The arrows in FIGS. 2A and 2B indicate fluid flow through the device. Negative pressure applied at the outlet 110 draws surrounding liquid through the membrane filter 135 and along the axial voids 140 toward the radial bores 125 that lead to the central channel 130. The device is bidirectional and negative pressure may alternatively be applied at the other outlet 110.

The membrane filter 135 can be molded as a cylindrical sleeve that may be drawn over the form 100, or may instead be a planar sheet that is wrapped around the form 100. Because of the closely spaced ribs 115 that it surrounds, the membrane filter 135 does not experience excessive bending or other radial strain despite the vacuum applied to its interior surface, and therefore need only be stiff enough to avoid collapse into the recesses between ribs 115 during operation. This facilitates use of a wide range of conventional filter materials, including cellulose ester, polyethersulfone, and cellulose acetate. As noted above, the support 100 may be assembled as a stacked sequence of segments 105 that may be screwed or otherwise sealably fitted together, affording a variable length that may be tailored to a particular application.

Figures 3, 4:
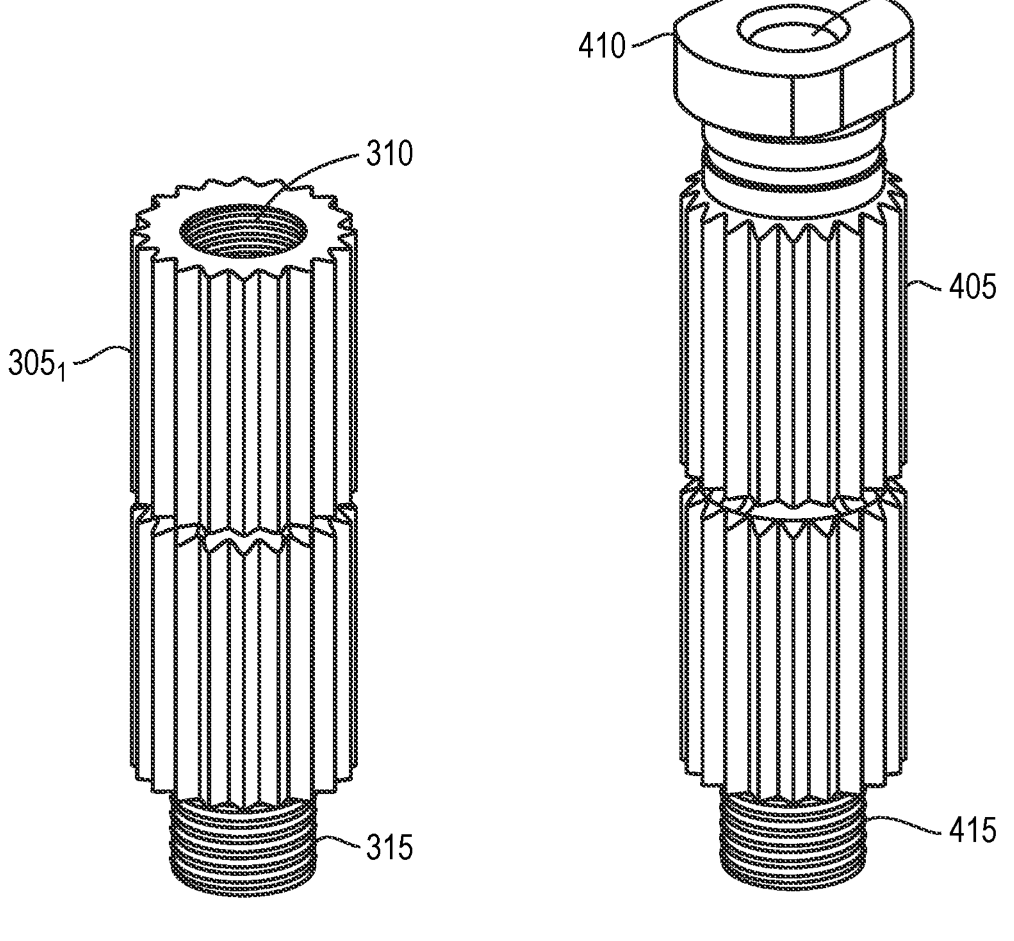
FIG. 3 is a perspective view of a middle segment of the support shown in FIG. 1.
FIG. 4 is a perspective view of an end segment of the support shown in FIG. 1.

As illustrated in FIG. 3, a middle segment 305$_1$ may include respective female and male threaded connectors 310, 315 and multiple such segments may be assembled in desired numbers between top and bottom segments to form the final support 100. The radially recessed annular regions 120 occur where two segments are connected; for example, the bores may extend through a flat (unthreaded) upper region of the male threaded connector 315.

A representative top segment 405 is shown in FIG. 4. The segment 405 may include respective terminal and male threaded connectors 410, 415. The terminal connector 410 facilitates fluid connection to the central interior channel 130. The optimal size of the segments 305$_1$, 405 relative to the overall length of a typical support 100 depends on the desired degree of design flexibility for users and the performance sensitivity to small changes in overall length. In general, the segments 305$_1$, 405 may range in length from 1 cm to 10 cm. A typical length of the overall support may range from from 5 cm to 50 cm.

Various other dimensions and parameters may be varied to suit particular applications. The interior diameter (ID)—i.e., the diameter of the central channel 130—determines the flow rate through the device. For example, it may be desirable to keep protein velocity at or below 2 m/s. Various embodiments utilize IDs ranging from 1 to 147 mm; a representative ID is 4 mm. The radial bores 125 may have diameters ranging from 1 mm to 5 mm. The number of bores through each radially recessed annular region 120 may typically range from one to 10, but larger devices may have 20 or more bores.

The outer diameter (OD) of the device 100 including the membrane filter 135 often represents a compromise between sufficient overall filter surface area (given the device length) and space constraints within a bioreactor. A representative (but non-limiting) minimum is 10 mm, and a typical value is 20 mm. The OD and ID may be considered together. The difference (i.e., the thickness of the support 100) must be adequate to support the pressure differential to which the support will be subjected. Increasing the ID:OD ratio means decreasing wall thickness, reducing mass and hence mechanical durability, but also reducing the pressure drop across the support. A representative range of ID:OD values is 0.1 to 0.95, with an optimal value of about 0.75.

The optimal overall device length may reflect application-related considerations (e.g., the size of a bioreactor, the amount of necessary surface area, etc.) as well as manufacturing considerations (e.g., assembly and heat sealing). Typical supports 100 may range in length from mm to 400 mm. Length may also be considered alongside OD, e.g., as a ratio. This ratio may range from as little as 1.0 to very high levels limited by bioreactor geometry and working liquid level. At this time a ratio of about 3.0 appears optimal.

The ribs 115 may be specified in terms of a depth (i.e., the height of the rib peak relative to the lowest point of the recession) and a width, or a ratio of depth to width. An optimal depth-to-width ratio is about 1.0, although values ranging from 0.1 to 15 are suitable. At a ratio of 1.0, the height of the peak is about the same as the width of the peak. This is the easiest form to manufacture (deep recesses can be hard to release from a mold intact). Ribs having a higher ratio may offer less mechanical stability and smaller flow channels, and may be more difficult to machine. A lower ratio means that a smaller amount of pressure-induced bowing of the filter material may reduce or eliminate flow through the channels. Typical depth values range from 0.1 mm to 10 mm, with about 1 mm being optimal in practical bioprocessing systems.

The number of ribs 115 may range from a low of three to higher values limited primarily by application, manufacturing and geometric (i.e., maintaining discreteness) considerations. The more ribs that are used for a given OD, the lower the flow will be between the membrane 135 and the support 100, but the greater the support that will be provided to the membrane to prevent collapse under pressure. The minimum number of ribs 115 for an application involving a given flow rate and pressure drop is that number which will prevent excessive bowing of the filter material into the axial voids 140 (i.e., bowing sufficient to retard flow).

The number of ribs 115 may also be considered as a ratio relative to the OD; that is, with the same rib geometry, the number of ribs distributed circumferentially around the support 100 may be varied. Optimally, as noted above, the channel width matches the rib width, corresponding to a ratio of 1.0 (or approximately 1.0). But this ratio may vary from, for example, 0.5 to 2, with smaller ratios producing larger flow channels and larger ratios resulting in smaller flow channels. In terms of performance, reducing the ratio is equivalent to decreasing the number of ribs, and increasing the ratio is equivalent to increasing the number of ribs.

The terms and expressions employed herein are used as terms and expressions of description and not of limitation, and there is no intention, in the use of such terms and expressions, of excluding any equivalents of the features shown and described or portions thereof. In addition, having described certain embodiments of the invention, it will be apparent to those of ordinary skill in the art that other embodiments incorporating the concepts disclosed herein may be used without departing from the spirit and scope of the invention. Accordingly, the described embodiments are to be considered in all respects as only illustrative and not restrictive.

What is claimed is:

1. A filter comprising:

an elongated element having a plurality of longitudinal segments, each having a plurality of axial ribs circumferentially distributed around an exterior portion thereof, the axial ribs having radial peaks and radial recessions therebetween, the elongated element being substantially nonporous, and adjacent longitudinal segments of the plurality of longitudinal segments are sealably fitted together in a stacked sequence;

a membrane filter medium wrapped as a planar sheet around the exterior portion of the elongated element and in contact with the elongated element at only the radial peaks of the axial ribs, thereby forming a plurality of axial voids between the radial recessions and the membrane filter medium;

a central channel extending axially through at least a portion of the elongated element and terminating in an outlet; and at least one radial channel fluidically coupling the axial voids to the central channel, whereby negative pressure at the outlet propagates through the axial voids to the membrane filter medium, wherein the plurality of axial ribs is interrupted by one or more annular regions between adjacent longitudinal segments of the plurality of longitudinal segments, the one or more annular regions radially recessed relative to the radial recessions of the plurality of axial ribs.

2. The filter of claim 1, wherein the at least one radial channel has a first end opening into the central channel and a second end opening into one of the one or more annular regions radially recessed relative to the ribs.

3. The filter of claim 2, wherein the annular region is unribbed.

4. The filter of claim 2, wherein the annular region has a plurality of circumferentially distributed radial channels therethrough.

5. The filter of claim 2, wherein the elongated element includes a plurality of unribbed annular regions each having a plurality of circumferentially distributed radial channel therethrough.

6. The filter of claim 1, wherein the filter medium is cellulose ester.

7. The filter of claim 1, wherein the filter medium is polyethersulfone.

8. The filter of claim 1, wherein the filter medium is cellulose acetate.

9. The filter of claim 1, wherein the filter medium is polyvinylidene fluoride.

10. The filter of claim 1, wherein the filter medium is polycarbonate.

11. The filter of claim 1, wherein the elongated element has a substantially circular cross-section.

12. The filter of claim 1, wherein the radial peaks each have (i) a radial height relative to the radial recessions and (b) a circumferential width, the radial height being approximately equal to the circumferential width.

13. The filter of claim 1, wherein the central channel has first diameter and the elongated element with the membrane filter medium wrapped therearound has a second diameter, a ratio of the first diameter to the second diameter ranging from 0.1 to 0.95.

14. The filter of claim 13, wherein the ratio of the first diameter to the second diameter is 0.75.

15. The filter of claim 1, wherein the elongated element has a length and the elongated element with the membrane filter medium wrapped therearound has a diameter, a ratio of the element length to the diameter being approximately 3.0.

* * * * *